United States Patent [19]
Kittelsen et al.

[11] Patent Number: 5,339,832
[45] Date of Patent: Aug. 23, 1994

[54] THERMOPLASTIC MOUTHGUARD WITH INTEGRAL SHOCK ABSORBING FRAMEWORK

[75] Inventors: Jon D. Kittelsen, Fridley; Paul C. Belvedere, Edina, both of Minn.

[73] Assignee: E-Z Gard Industries, Inc., Minneapolis, Minn.

[21] Appl. No.: 66,469

[22] Filed: May 24, 1993

[51] Int. Cl.$^5$ .................................................. A61F 5/14
[52] U.S. Cl. ........................................ 128/862; 128/861; 128/859
[58] Field of Search ..................... 128/862, 861, 859

[56] References Cited

U.S. PATENT DOCUMENTS

| | | | |
|---|---|---|---|
| 2,630,117 | 3/1953 | Coleman | 128/136 |
| 2,678,043 | 5/1954 | Stark | 128/861 |
| 2,702,032 | 2/1955 | Freedland | 128/861 |
| 3,223,085 | 12/1965 | Gores et al. | 128/136 |
| 3,247,844 | 4/1966 | Berghash | 128/136 |
| 3,411,501 | 11/1968 | Greenberg | 128/136 |
| 3,485,242 | 12/1969 | Greenberg | 128/136 |
| 3,496,936 | 2/1970 | Gores | 128/136 |
| 3,505,995 | 4/1970 | Greenberg | 128/862 |
| 3,513,838 | 5/1970 | Foderick et al. | 128/136 |
| 3,692,025 | 9/1972 | Greenberg | 128/136 |
| 3,864,832 | 2/1975 | Carlson | 32/40 B |
| 3,943,924 | 3/1976 | Kallestad et al. | 128/136 |
| 4,337,765 | 7/1982 | Zimmerman | 128/136 |
| 4,672,959 | 6/1987 | May et al. | 128/136 |
| 4,765,324 | 8/1988 | Lake, Jr. | 128/861 |
| 5,152,301 | 10/1992 | Kittelsen et al. | 128/861 |
| 5,235,991 | 8/1993 | Minneman | 128/859 |

OTHER PUBLICATIONS

American Dental Association. "Give Your Teeth A Sporting Chance," 1985.
Stephen D. Smith, D. M. D. "Muscular Strength Correlated To Jaw Posture and the Temporomandibular Joint," *NYS Dental Journal.* Aug.-Sep. 1978.
W. B. May, D.D.S. "Reduction of Stress in the Chewing Mechanism Part III." *Basal Facts.* vol. 3, No. 1.

*Primary Examiner*—Robert A. Hafer
*Assistant Examiner*—Michael O'Neill
*Attorney, Agent, or Firm*—Palmatier, Sjoquist & Helget

[57] ABSTRACT

A composite mouthguard has a flexible and tough, softenable thermoplastic mouthguard portion with a U-shaped base having upward inner lingual and outer labial walls extending from the base. A shock absorbing and attenuating nonsoftening, resilient, low compression, elastomer framework is embedded in the mouthguard portion to absorb, attenuate and dissipate shock forces exerted on the mouthguard during athletic activity.

23 Claims, 3 Drawing Sheets

THERMOPLASTIC MOUTHGUARD WITH INTEGRAL SHOCK ABSORBING FRAMEWORK

BACKGROUND OF THE INVENTION

This invention relates generally to a protective mouthguard for use by athletes, and more particularly to a composite mouthguard that absorbs, attenuates and dissipates shock forces exerted on the mouthguard with additional teeth, jaw and joint protecting features and which further increases body muscular strength and endurance.

A number of mouthguards currently exist in the art for protecting the teeth and for reducing the chance of shock, concussions and other injuries as a result of high impact collisions and blows during athletic competition. Mouthguards generally are characterized as being nonpersonalized, universal and stock model type, or are custom formed to have upper jaw and teeth direct contact. Additionally, mouthguards may be tethered or untethered. Tethered mouthguards are usually connected to a fastening point, such as a helmet or face guard, to prevent the chance of the mouthguard from being lost as well as to prevent swallowing of the mouthguard or choking on the mouthguard by the user.

Failure to use a mouthguard or the use of an improperly fitted mouthguard when impacts, collisions or blows occur to the jaw structure of an athlete have recently been found to be responsible for athletes' susceptibility to headaches, presence of earaches, ringing in the ears, clogged ears, vertigo, concussions and dizziness. The cause of these types of health problems and injuries are generally not visible by inspection of the mouth or jaw, but more particularly relate to the temporomandibular joint (TMJ) and surrounding tissues where the lower jaw is connected to the skull in the proximity where the auriculo-temporalis nerves and supra-temporal arteries pass from the neck nerves into the skull to the brain.

Most mouthguards in the past have been made from ethylene vinyl acetate (EVA). The material has a softening point approximating the temperature of boiling water which will permit the mouthguard to be placed in boiling water and custom fit to the wearer's mouth. However, the EVA material, although the best known to date, is not ideal for absorption, attenuation and dissipation of shock forces exerted on the EVA mouthguard during athletic activity. Furthermore, the EVA material is subject to deformation and break down with continued use and chewing thereon by the wearer.

There is a need for a mouthguard that may be fit by the user, practitioners, dentists, equipment personnel and trainers that will custom fit with direct contact with the upper jaw's teeth. Such a mouthguard should absorb, attenuate and dissipate shock forces exerted on the mouthguard during athletic activity, permit a positioning of the lower jaw into the power position for increased endurance and muscular power, will facilitate breathing and speech, and will reduce pressure and possible concussion impact upon the cartilage of the joint, the joint itself, the arteries and the nerves in proximity of the joints.

SUMMARY OF THE INVENTION

A composite mouthguard has a flexible and tough, softenable thermoplastic mouthguard portion with a U-shaped base having upward inner lingual and outer labial walls extending therefrom. A shock absorbing and attenuating nonsoftening, resilient, low compression, elastomer framework is embedded in the mouthguard portion to absorb, attenuate and dissipate shock forces exerted on the mouthguard during athletic activity.

A principal object and advantage of the present invention is that the mouthguard is of a composite construction permitting the formation of a customized thermoplastic mouthguard portion protecting the teeth, jaws and gums with an internal, shock absorbing, nonsoftening, resilient, low compression, elastomeric framework therein to further absorb, attenuate and dissipate shock forces exerted on the mouthguard.

Another object and advantage of the present invention is the elastomeric framework may begin as an anterior impact brace on the anterior portion of the mouthguard contacting the anterior teeth and extending through the base portion of the mouthguard forming cushioning pads in the occlusal regions for the posterior teeth to absorb, attenuate and dissipate shock as heretofore not known.

Another object and advantage of the present invention is that the posterior cushion pads of the framework may have enlarged portions which assist in custom fitting of the lower jaw to the power position as well as further providing the advantage of absorption, attenuation and dissipation of shock.

Another object and advantage of the present invention is that the composite material with the elastomeric framework within the thermoplastic mouthguard portion will resist wear and break down of the mouthguard otherwise associated with EVA mouthguards.

Another object and advantage of the present invention is that the elastomeric framework, which is not softened under boiling water, will permit the appropriate power positioning of the lower jaw despite the softening of the thermoplastic mouthguard portion, thereby assuring proper fitting of the composite mouthguard.

Another object and advantage of the present invention is that the elastomeric framework has enlarged portions and an anterior impact brace within the thermoplastic mouthguard portion where shock forces are most likely to be exerted upon the mouthguard for resilient absorption, attenuation and dissipation of shock forces.

Another object and advantage of the present invention is that occlusal thermoplastic posterior pads may be included in the mouthguard portion wherein the elastomeric framework may be embedded to provide the absorption, attenuation and shock dissipation qualities as well as permitting the mouthguard and lower jaw to be formed and placed in the power position moving the condyle downwardly and forwardly away from the nerves and arteries within the fossae or socket to increase body muscular strength, greater endurance and improved performance by the mouthguard user.

Other objects and advantages will become obvious with a reading of the following specification and appended claims with a review of the FIGURES.

DETAILED SPECIFICATION

Figures 1, 1A:
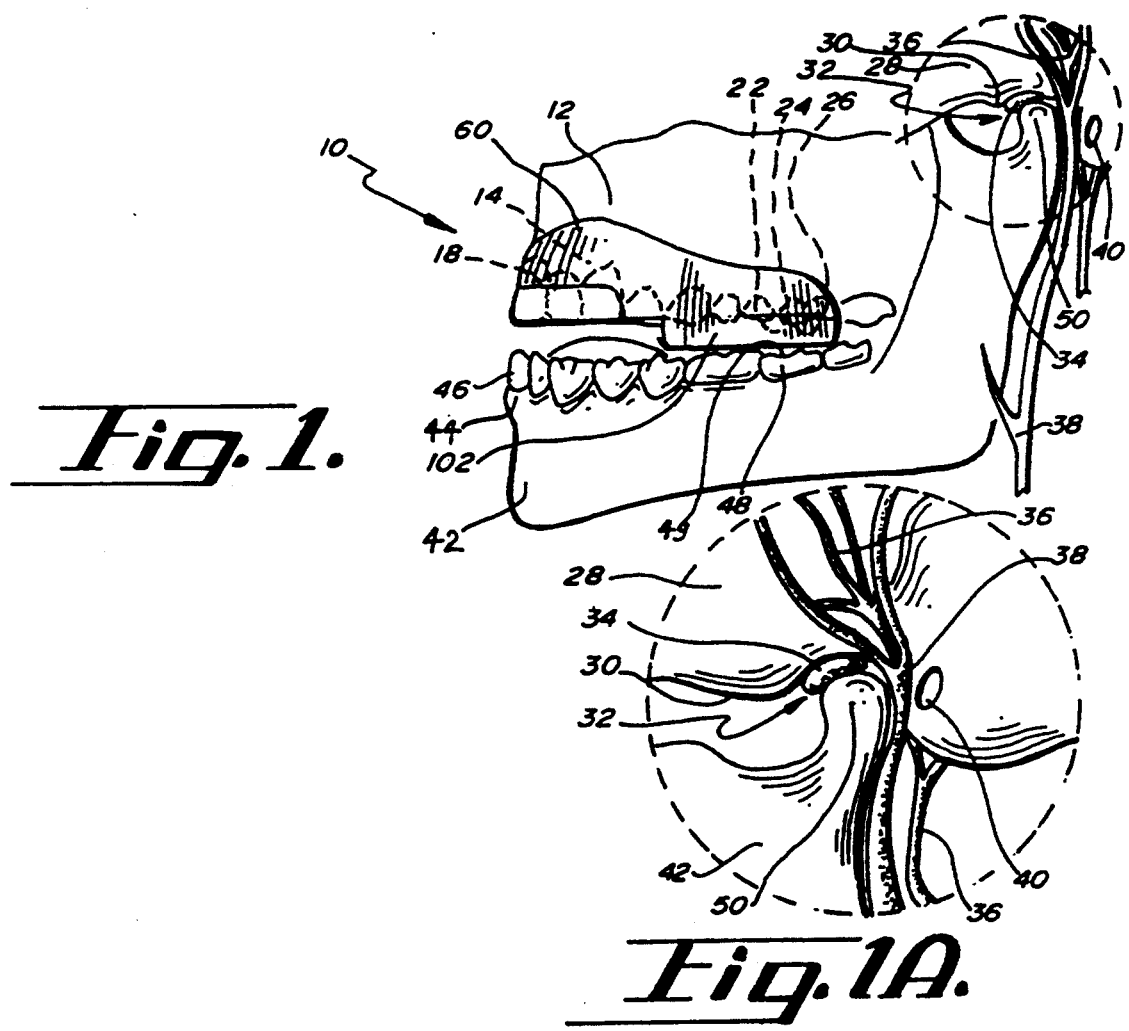
FIG. 1 is a maxillary mandibular buccal or partial side elevational view of the jaws and temporomandibular joint of a user of a mouthguard of the present invention.
FIG. 1A is an enlarged view of the circled temporomandibular joint portion of FIG. 1.
Figure 2:
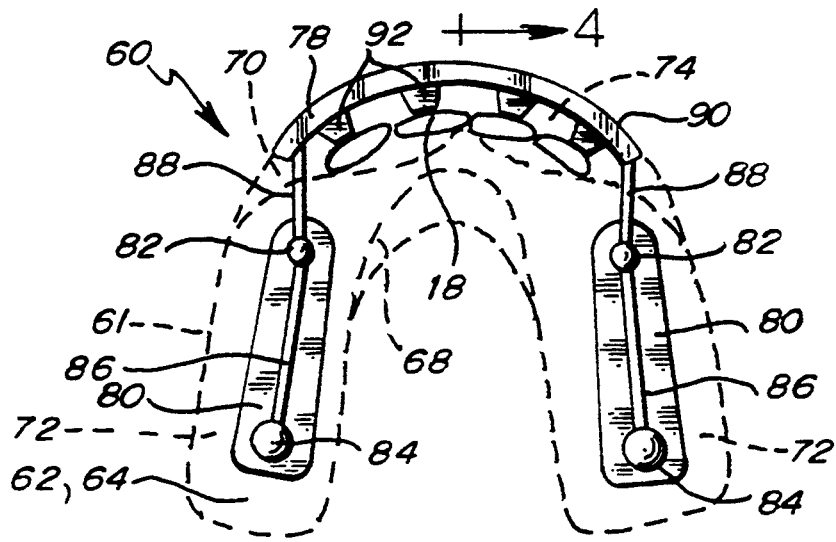
FIG. 2 is a top plan view of the composite mouthguard showing the anterior teeth contacting the anterior cushioning pads of the anterior impact brace of the elastomeric framework with the thermoplastic mouthguard portion shown in phantom outline.

To understand the structural features and benefits of the mouthguard 60 of the present invention, some anatomy will first be described. Referring to FIGS. 1 and 1A, the mouthguard user would have a mouth 10, generally comprised of a rigid upper jaw 12 and a movable lower jaw 42 which are movably connected at the temporomandibular joint (TMJ) 32 and 50.

More specifically, the rigid upper jaw 12 has gum tissue 14 within mouth 10. Gum tissue 14, as well as the bone thereunder, support anterior teeth (incisors and canines) 18 which have incisal or biting surfaces. The gum tissues 14 and the bone thereunder also support posterior teeth (molars and bicuspids) 22 which have cusps and biting surfaces 26.

Referring to one side of the human head, the temporal bone 28 is located upwardly and rearwardly of the upper jaw 12 and is in the range of 1/16 to 1/32 inch thick. The articular eminence 30 forms the beginning of the fossa 32 or the socket of the temporomandibular joint 32 and 50. Rearwardly and posteriorly to the articular eminence 30 is located cartilage 34. Through the temporomandibular joint 32 and 50 pass the auriculo-temporalis nerve 36 and the supra-temporal artery. Posteriorly to this structure is located the inner ear.

The movable jaw or mandible 42 supports a bone covered by gum tissue 44 which further supports anterior teeth (incisors and canines) 46 and posterior teeth (molars and bicuspids) 48 with occlusal surfaces 52. The condyle 50 of the lower jaw 42 forms the ball of the temporomandibular joint 32 and 50. This anatomical structure is the same for both sides of the head.

Repeated impacts, collisions, blows or forces exerted on the movable lower jaw 42 result in excessive wearing forces upon the condyle 50 and the cartilage or disc 34 - typically resulting in deterioration or slippage of the cartilage 34. Thereafter, the lower jaw 42 may be subject to irregular movement, loss of comfortable range of movement and clicking of the joint 32 and 50.

The auriculo-temporalis nerve 36 relates to both sensory and motor activities of the body. Any impingement or pinching of this nerve 36 can result in health problems as previously mentioned. The supra-temporal artery 38 is important in that it provides blood circulation to the head. Impingement, pinching, rupture or blockage of this artery 38 will result in possible loss of consciousness and reduced physical ability and endurance due to the restriction of blood flow to the brain. Thus, it is extremely important to assure that the condyle 50 does not impinge upon the auriculo-temporalis nerve 36 or the supra-temporal artery 38.

It is also important to note that the temporal bone 28 is not too thick. Medical science has known that a sharp shock or concussive force applied to the lower jaw 42 possibly could result in the condyle 50 protruding through the temporal bone 28 thereby causing death. This incident rarely, but sometimes, occurs with respect to boxing athletes.

Referring to FIGS. 2–6, the composite mouthguard may be generally seen. Mouthguard 60 is comprised of a thermoplastic mouthguard portion 61, which is generally horse shoe or U-shaped, with the embedded or substantially internal elastomeric framework 78 forming posterior cushion pads 80 and an anterior impact brace 90.

More particularly, the thermoplastic mouthguard portion 61 suitably may be made of copolymers of ethylene and vinyl acetate, such as ethylene vinyl acetate (EVA) which is commercially available and approved for oral use by the Food and Drug Administration. The thermoplastic mouthguard portion 61 has a U-shaped base 62 with a top side 64 and a bottom side 66. Extending upwardly are inner lingual and outer labial walls 68 and 70 forming a channel therebetween for receiving the upper jaw and teeth 12, 18 and 22. The thermoplastic mouthguard portion 61 has a posterior portion 72 and an anterior portion 74.

Located along the bottom side 66 of the posterior portion 72 of the U-shaped base 62 may be located optional thermoplastic occlusal posterior pads 76. These thermoplastic occlusal posterior pads 76 space apart the anterior teeth 46 of the lower jaw 42 from the anterior portion 74 of the bottom side 66 of the U-shaped base 62. This arrangement facilitates breathing and speech, and lessens condyle 50 pressure and impact upon the cartilage 34, the temporomandibular joints 32 and 50, the arteries 38 and the nerves 36.

The optional occlusal posterior pads 76 also permit the lower jaw 42 to be positioned forwardly and anteriorly in a range of 1 to 4 millimeters depending upon the desired position to assume the power position allowing the most freedom and least amount of potential impingement to the TMJ 32 and 50 and surrounding tissues.

The elastomeric framework 78 suitably is made of an elastomer, which unlike copolymers of ethylene and vinyl acetate, exhibits a high resilience, low compression, shape maintenance and shock absorption, attenuation and dissipation. Virtually all rubbers that exhibit these physical characteristics may be utilized for the elastomeric framework 78, including vulcanized rubber. Applicant has found a thermoplastic rubber marketed under the trademark KRATON ® works well, which is marketed by GLS Plastics of 740B Industrial Drive, Cary, Illinois 60013. This thermoplastic rubber is unique in that it is injection moldable, FDA approved and readily adheres with copolymers of ethylene and vinyl acetate. Furthermore, the thermoplastic rubber has a melting or softening point significantly higher than that of EVA.

Consequently, the elastomeric framework 78 is initially molded or formed afterwhich the thermoplastic mouthguard portion 61 may be injection molded therearound.

Figure 6:
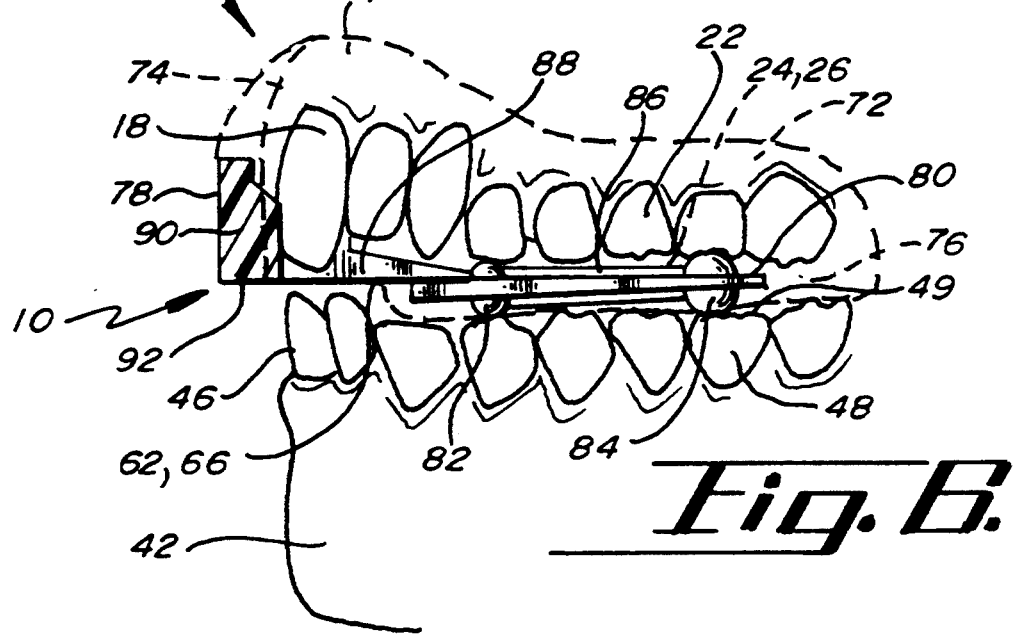
FIG. 6 is a partial side elevational view of the jaws similar to FIG. 1 with the elastomeric framework of the composite mouthguard partially broken away and the thermoplastic mouthguard shown in phantom outline.
Figure 3:
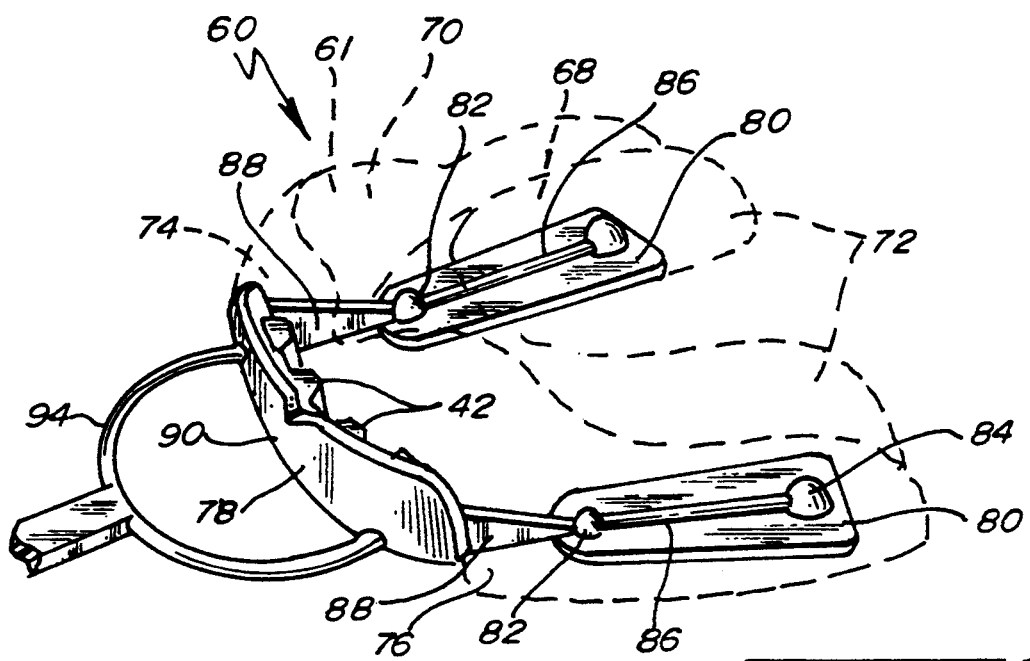
FIG. 3 is a perspective view of the composite mouthguard showing the elastomeric framework connected to a wishbone tether with the thermoplastic mouthguard portion shown in phantom outline therearound.
Figure 5:
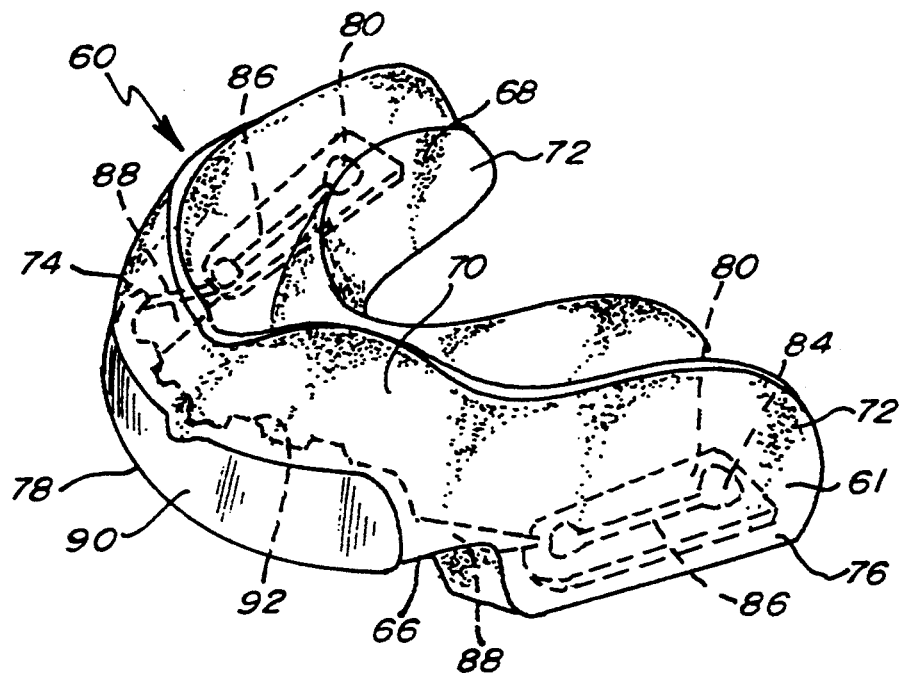
FIG. 5 is a perspective view of the composite mouthguard with portions of the elastomeric framework shown in phantom outline.

The elastomeric framework 78 has posterior cushion pads 80 which suitably lay within the posterior portions 72 of the U-shaped base 62. Alternatively, the posterior cushion pads may be embedded within the occlusal posterior pads 76 or between the pads 76 and the U-shaped anterior base portions 62. The posterior cushion pads 80 suitably have enlarged portions 82 and 84 suitably in the bicuspid and molar regions of the teeth. The enlarged portions may take the form of spheres, columns, or knobs. The enlarged molar portions or spheres 84 are suitably positioned to fit in the area of the first adult molars as shown in FIG. 6. The bicuspid enlarged portions 82 appropriately fit on the bicuspid teeth adjacent the canine or eyeteeth.

The posterior cushion pads 80 together with the enlarged portions 82 and 84 cause the mandible or lower jaw 42 to slide forwardly and slightly downwardly while fitting the composite mouthguard 60. Also, the condyles 50 are moved downwardly and away from the fossae or sockets 32 without the need for exotic devices and/or measurements, articulation, etc. Furthermore, the posterior cushion pads 80 with the enlarged portions 82 and 84 assure proper fitting of the composite mouthguard 50 when softened by prohibiting the user from biting too deeply into the soft EVA material of the thermoplastic mouthguard portion 61. Also, the bicuspid enlarged portions 82 assure that there is no excessive upward displacement of the anterior portions of the lower movable jaw or mandible 42.

A raised ridge 86 on top and bottom of the posterior cushion pad 80 connects the enlarged portions 82 and 84. This ridge 86 has been found to force the softened EVA material of the thermoplastic mouthguard portion 61 to remain in the occlusal biting surfaces or grooves 26 while fitting.

Figure 4:
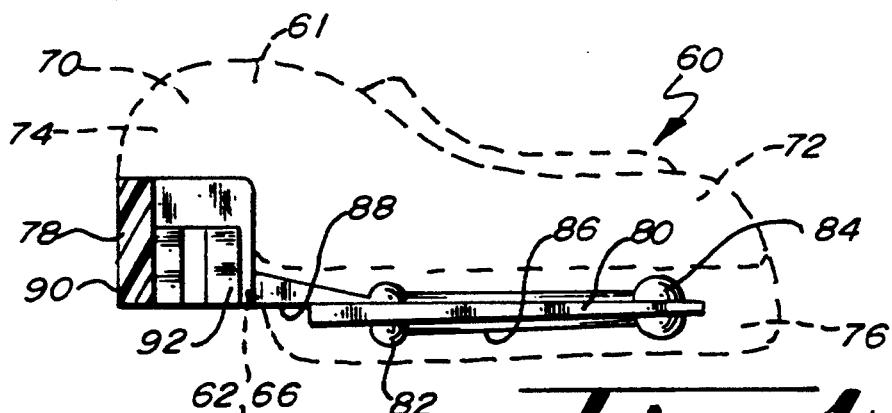
FIG. 4 is a cross-sectional view taken along lines 4—4 of FIG. 2.

Moving forwardly, a transition support portion 88 extends forwardly from the posterior cushion pads 80 and connects to the anterior impact brace 90. Anterior impact brace 90 has protruding anterior cushion pads 92 which extend through the upward outer labial wall 70 to actually contact the anterior teeth 18 of the upper jaw 12 as clearly shown in FIG. 2 to advantageously absorb, attenuate and dissipate shock exerted thereat. FIGS. 4 and 6 show double phantom lines without cross sectioning in the anterior portion 74 of the thermoplastic mouthguard portion 61 to illustrate that the copolymer mouthguard portion 61 at least partially surrounds the anterior cushion pads 92 to further embed the framework 78 in the anterior portion 74 of the mouthguard portion 61. The anterior cushion pads 92 extend rearwardly through the anterior portion 74 of the outer labial wall 70. A wishbone tether 94 (FIG. 3) suitably may be utilized with the composite mouthguard 60 and is the subject of Applicant's co-pending application.

In operation, the composite mouthguard 60 may be momentarily submersed suitably into boiling water. Thereafter, the mouthguard 60 is immediately placed onto the teeth 18 and 22 of the upper jaw 12. Next, the lower jaw 42 is positioned forwardly or anteriorly in a range of 1 to 4 millimeters as the posterior teeth 48 engage the enlarged portions 82 and 84 with or without occlusal posterior pads 76. The wearer or user then applies suction between the upper jaw 12 and the mouthguard 60 while packing the mouthguard 60 with the hands along the cheeks and lips adjacent the anterior and posterior teeth 18 and 22 of the upper jaw 12. The posterior teeth 48 of the lower jaw 42 will properly index upon the bottom surface of the occlusal posterior pads 76 or the posterior portion 72 of the U-shaped base 62.

The user of the composite mouthguard will have correct jaw posture for athletic participation which will assure minimal impact injury to the TMJ 32 and 50 as well as the surrounding tissues, teeth and respective jaws. The elastomeric framework 78 with its component parts will absorb, attenuate and dissipate shock forces as heretofore not known. Furthermore, the user will experience increased endurance, performance and muscular freedom due to the power positioning and posture of the TMJ joints 32 and 50.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

We claim:

1. A composite mouthguard for a user having an upper jaw with anterior teeth, posterior teeth with occlusal surfaces, and fossae with cartilage forming sockets, and a movable lower jaw with anterior teeth, posterior teeth with occlusal surfaces and condyles movably fitted within the sockets forming the temporomandibular joints through which the auriculo-temporalis nerves and supra-temporal arteries pass, the mouthguard comprising:

(a) a flexible and tough mouthguard portion made of a first material of a softenable thermoplastic having an U-shaped base with top and bottom sides with upward inner lingual and outer labial walls and further having posterior and anterior portions; and (b) a shock absorbing and attenuating framework made of a second material of a nonsoftening, resilient, low compression elastomer which is embedded in the mouthguard posterior portions of the mouthguard base comprised of a posterior cushion pad in each posterior portion wherein the elastomeric framework extends forwardly from the posterior cushion pads to form an anterior impact brace on the anterior portion of the upward outer labial wall and at least partially extends through the labial wall to form anterior cushion pads to touch the anterior teeth of the upper jaw to absorb, attenuate and dissipate shock forces exerted on the mouthguard during athletic activity.

2. A composite mouthguard for a user having an upper jaw with anterior teeth, posterior teeth with occlusal surfaces, and fossae with cartilage forming sockets, and a movable lower jaw with anterior teeth, posterior teeth with occlusal surfaces and condyles movably fitted within the sockets forming the temporomandibular joints through which the auriculo-temporalis nerves and supra-temporal arteries pass, the mouthguard comprising:

(a) a flexible and tough mouthguard portion made of a first material of a softenable thermoplastic having an U-shaped base with top and bottom sides with upward inner lingual and outer labial walls and further having posterior and anterior portions; and (b) a shock absorbing and attenuating framework made of a second material of a nonsoftening, resilient, low compression elastomer which is embedded in the mouthguard posterior portions of the mouthguard base comprised of a posterior cushion pad in each posterior portion each with enlarged portions in an area of a molar tooth and a bicuspid tooth to absorb, attenuate and dissipate shock forces exerted on the mouthguard during athletic activity.

3. The composite mouthguard of claim 2, further comprising a raised ridge on each posterior cushion pad extending from the enlarged portions.

4. The composite mouthguard of claim 2, further comprising thermoplastic occlusal poster pads on the bottom side of the base along only the posterior portions to space apart the anterior teeth of the lower jaw from the anterior portion of the bottom side of the U-shaped base to facilitate breathing and speech and to lessen condyles pressure and impact upon the cartilage, and temporomandibular joints, the arteries and the nerves.

5. The composite mouthguard of claim 4, wherein the elastomeric posterior cushion pads are embedded in the thermoplastic occlusal posterior pads.

6. The composite mouthguard of claim 2, wherein the framework extends outwardly from the posterior cushion pads to form an anterior impact brace on the anterior portion of the upward outer labial wall and at least partially extends through the labial wall to form anterior cushion pads to touch the anterior teeth of the upper law.

7. The composite mouthguard of claim 2, wherein the mouthguard portion first material is made from a thermoplastic comprised of copolymers of ethylene or vinyl acetate.

8. The composite mouthguard of claim 2, wherein the framework second material is made from an elastomeric material of a group comprising thermoplastic rubber or vulcanized rubber.

9. A composite mouthguard for a user having an upper jaw with anterior teeth, posterior teeth with occlusal surfaces, and fossae with cartilage forming sockets, and a movable lower jaw with anterior teeth, posterior teeth with occlusal surfaces and condyles movably fitted within the sockets forming the temporomandibular joints through which the auriculo-temporalis nerves and supra-temporal arteries pass, the mouthguard comprising:
  (a) a flexible and tough, softenable thermoplastic mouthguard portion having an U-shaped base with top and bottom sides with upward inner lingual and outer labial walls and further having posterior and anterior portions; and
  (b) a shock absorbing and attenuating nonsoftening, resilient, low compression, elastomeric framework embedded in the mouthguard portion to absorb, attenuate and dissipate shock forces exerted on the mouthguard during athletic activity, wherein the elastomeric framework forms an anterior impact brace on the anterior portion of the upward outer labial wall and extends rearwardly to form posterior cushion pads in the posterior portions of the mouthguard base and wherein the anterior impact brace at least partially extends through the labial wall to form anterior cushion pads to touch the anterior teeth of the upper jaw.

10. The composite mouthguard of claim 9, wherein each posterior cushion pad has an enlarged portion above and below the cushion pad in an area of a molar tooth.

11. The composite mouthguard of claim 10, wherein each posterior cushion pad has a second enlarged portion in an area of a bicuspid tooth.

12. The composite mouthguard of claim 9, wherein each posterior cushion pad has two enlarged portions above and below the cushion pad in areas of molar and bicuspid teeth.

13. The composite mouthguard of claim 12, further comprising a raised ridge on each posterior cushion pad extending from the enlarged portions.

14. The composite mouthguard of claim 9, further comprising thermoplastic occlusal poster pads on the bottom side of the base along only the posterior portions to space apart the anterior teeth of the lower jaw from the anterior portion of the bottom side of the U-shaped base to facilitate breathing and speech and to lessen condyles pressure and impact upon the cartilage, and temporomandibular joints, the arteries and the nerves.

15. The composite mouthguard of claim 14, wherein the elastomeric posterior cushion pads are embedded in the thermoplastic occlusal posterior pads.

16. The composite mouthguard of claim 9, wherein the thermoplastic mouthguard is made from copolymers of ethylene or vinyl acetate.

17. The composite mouthguard of claim 9, wherein the elastomeric framework is made from a material of a group comprising thermoplastic rubber or vulcanized rubber.

18. A composite mouthguard for a user having an upper jaw with anterior teeth, posterior teeth with occlusal surfaces, and fossae with cartilage forming sockets, and a movable lower jaw with anterior teeth, posterior teeth with occlusal surfaces and condyles movably fitted within the sockets forming the temporomandibular joints through which the auriculo-temporalis nerves and supra-temporal arteries pass, the mouthguard comprising:
  (a) a flexible and tough, softenable thermoplastic mouthguard portion having an U-shaped base with top and bottom sides with upward inner lingual and outer labial walls and further having posterior and anterior portions;
  (b) a shock absorbing and attenuating non-softening, resilient, low compression, elastomeric framework embedded in the mouthguard portion to absorb, attenuate and dissipate shock forces exerted on the mouthguard during athletic activity, wherein the elastomeric framework forms an anterior impact brace on the anterior portion of the upward outer labial wall and extends rearwardly to form posterior cushion pads in the posterior portions of the mouthguard base;
  (c) two enlarged portions on each posterior cushion pad in areas of bicuspid and molar teeth; and
  (d) anterior cushion pads on the anterior impact brace extending rearwardly through the labial wall to touch the anterior teeth of the upper jaw.

19. The composite mouthguard of claim 18, further comprising a raised ridge on each posterior cushion pad extending from the enlarged portions.

20. The composite mouthguard of claim 18, further comprising thermoplastic occlusal poster pads on the bottom side of the base along only the posterior portions to space apart the anterior teeth of the lower jaw from the anterior portion of the bottom side of the U-shaped base to facilitate breathing and speech and to lessen condyles pressure and impact upon the cartilage, and temporomandibular joints, the arteries and the nerves.

21. The composite mouthguard of claim 20, wherein the elastomeric posterior cushion pads are embedded in the thermoplastic occlusal posterior pads.

22. The composite mouthguard of claim 18, wherein the thermoplastic mouthguard is made from copolymers of ethylene or vinyl acetate.

23. The composite mouthguard of claim 18, wherein the elastomeric framework is made from a material of a group comprising thermoplastic rubber or vulcanized rubber.

* * * * *